(12) United States Patent
Cantat et al.

(10) Patent No.: US 9,133,135 B2
(45) Date of Patent: Sep. 15, 2015

(54) METHOD FOR PREPARING NITROGEN COMPOUNDS

(71) Applicant: Commissariat A L'Energie Atomique Et Aux Energies Alternatives, Paris (FR)

(72) Inventors: Thibault Cantat, Issy les Moulineaux (FR); Christophe Gomes, Antony (FR); Olivier Jacquet, Orsay (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/404,885

(22) PCT Filed: Jun. 4, 2013

(86) PCT No.: PCT/IB2013/054601
§ 371 (c)(1),
(2) Date: Dec. 1, 2014

(87) PCT Pub. No.: WO2013/182993
PCT Pub. Date: Dec. 12, 2013

(65) Prior Publication Data
US 2015/0148535 A1 May 28, 2015

(30) Foreign Application Priority Data
Jun. 5, 2012 (FR) ..................................... 12 55238

(51) Int. Cl.
| | | |
|---|---|---|
| C07D 235/06 | (2006.01) | |
| C07D 239/70 | (2006.01) | |
| C07D 239/74 | (2006.01) | |
| C07D 239/88 | (2006.01) | |
| C07C 257/12 | (2006.01) | |

(52) U.S. Cl.
CPC ............ C07D 239/88 (2013.01); C07C 257/12 (2013.01); C07D 235/06 (2013.01); C07D 239/70 (2013.01); C07D 239/74 (2013.01)

(58) Field of Classification Search
CPC .. C07C 257/12; C07D 235/06; C07D 239/70; C07D 239/74; C07D 239/88
See application file for complete search history.

(56) References Cited

FOREIGN PATENT DOCUMENTS

EP 0 652 202 A1 5/1995

OTHER PUBLICATIONS

Alinezhad, et al., Synthesis of Benzimidazole Derivatives Using Heterogeneous ZnO Nanoparticles, Synthetic Communications, 42(1), pp. 102-108 (2012).*

International Search Report and Written Opinion from International Application No. PCT/IB2013/054601 dated Oct. 16, 2013.
Alinezhad, Heshmatollah et al.; Synthesis of Benzimidazole Derivatives Using Heterogenous ZnO Nanoparticles; Synthetic Communications; vol. 42, No. 1; Jan. 2012; pp. 102-108; XP002686063.
Weith, W.; "Methenyldiphenyldiamine"; Chemische Berichte; vol. 9; 1876; pp. 454-463; XP002686064.
Dibenedetto, Angela et al.; "Reaction of Silylalkylmono- and Silylalkyldi-amines with Carbon Dioxide: Evidence of Formation of Inter- and Intra-Molecular Ammonium Carbamates of Industrial Interest Under Carbon Dioxide Catalysis"; Green Chemistry; vol. 4, No. 5; Jul. 29, 2002; pp. 439-443; XP055009762.
Sakakura, Toshiyasu, et al.; "Transformation of Carbon Dioxide"; Chemical Reviews; vol. 107, No. 6; Jun. 1, 2007; pp. 2365-2387; XP002657706.
Morris A J et al.; Accounts Chem. Res., 2009, 42 (1983).
Berkefeld, A., et al.; J Am. Chem. Soc., 2010, 132: 10660.
Gall, et al.; Jorunal of Medicinal Chemistry; 1988, 31: 1816-1820.
Enthaler, S, et al.; European Journal of Organic Chemistry; 2010, #25, pp. 4893-4901.
Cheng, K.M. et al.; Bioorganic and Medicinal Chemistry Letters, 2010, vol. 20, #22, pp. 6781-6784.
Mekhalfia, A., et al.; Tetrahedron, vol. 62, #24, pp. 5617-5625.
Khasksar, Samad, et al.; Journal of Fluorine Chemistry, 2010, vol. 131, No. 12; pp. 1377-1381.
Smith C L et al.; Journal of Organometallic Chemistry, 81 (1974) pp. 33-40.
Homer G D et al.; Journal of the American Chemical Society; 95, 23 (1973) pp. 7700-7707.
Spialter L et al.; Journal of the American Chemical Society; 93, 22 (1971) pp. 5682-5686.
West R; Jouranl of the American Chemical Society (1954) pp. 6015-6017.
Pleiss U et al.; "Synthesis and and Applications of Isotopically Labelled Compounds"; vol. 7, Wiley-WCH; 2001.
Voges R et al.; "Preparation of Compounds Labeled with Tritium and Carbon-14", Wiley-WCH, Chippenham (UK) 2009.
Kim Yong-Joo et al.; J. Org. Chem.; 1991, 56; pp. 4435-4439.
Dinsmore, Christopher J., et al.; Organic Letters, 2004, vol. 6, No. 17; pp. 2885-2888.
Groves, John T.; J. Am. Chem. Soc., 1988, 110; pp. 8443-8452.

(Continued)

Primary Examiner — Erich A Leeser
(74) Attorney, Agent, or Firm — Alston & Bird LLP

(57) ABSTRACT

The present invention relates to a method for preparing nitrogen compounds using carbon dioxide, and to the use of the method in the production of vitamins, pharmaceutical products, adhesives, acrylic fibers, synthetic leathers, pesticides, herbicides, antifungal agents and fertilizers. The invention also relates to a method for producing vitamins, pharmaceutical products, adhesives, acrylic fibers, synthetic leathers, pesticides, herbicides, antifungal agents and fertilizers, which includes a step of preparing nitrogen compounds using the method of the invention. The invention further relates to a method for preparing labelled nitrogen compounds using carbon dioxide and to the uses thereof.

20 Claims, 1 Drawing Sheet

(56) References Cited

OTHER PUBLICATIONS

Kochina T A et al.; *Russian Jouranl of General Chemistry*; vol. 72, No. 8; 2002; pp. 1222-1224.

Shishigin E A et al.; *Russian Journal of General Chemistry*; vol. 75, No. 1; 2005; pp. 152.

Ho, J.Z., et al.; *Helvetic Chimica Acta*, 2005, 88; p. 1040.

Ekhato, I.V., et al.; *J. Label. Compd. Radiopharm.*, 2011, 54; pp. 202-205.

Chan, Kenneth K., et al.; *Journal of Medicinal Chemistry*, 1977, vol. 20, No. 4; p. 598.

Berkefeld A., et al.; *J. Am. Chem. Soc.*, 2010, 132: 10660.

Gall, et al.; *Journal of Medicinal Chemistry*; 1988, 31: 1816-1820.

West R; *Journal of the American Chemical Society* (1954) pp. 6015-6017.

Pleiss U et al.; "Synthesis and Applications of Isotopically Labelled Compounds"; vol. 7, *Wiley-WCH*; 2001.

Kochina T A et al.; *Russian Journal of General Chemistry*; vol. 72, No. 8; 2002; pp. 1222-1224.

\* cited by examiner

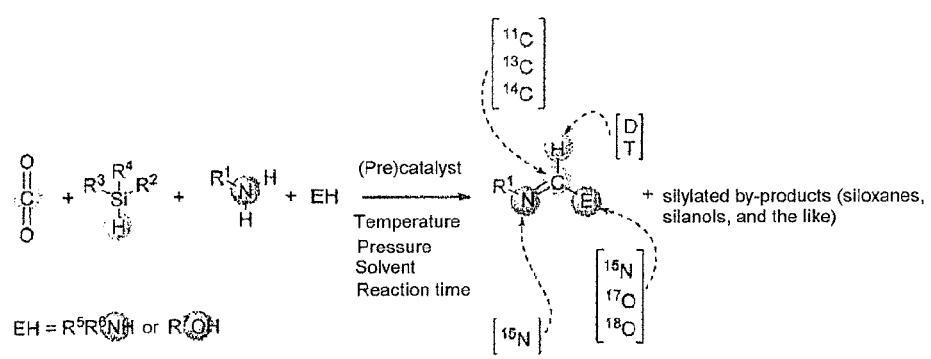

METHOD FOR PREPARING NITROGEN COMPOUNDS

FIELD

The present invention relates to a process for the preparation of nitrogenous compounds using carbon dioxide and to the use of this process in the manufacture of vitamins, pharmaceutical products, adhesives, acrylic fibers, synthetic leather, pesticides, herbicides, antifungals and fertilizers.

The present invention additionally relates to a process for the preparation of labeled nitrogenous compounds using carbon dioxide and to their uses.

It also relates to a process for manufacture of vitamins, pharmaceutical products, adhesives, acrylic fibers, synthetic leather, pesticides, herbicides, antifungals and fertilizers comprising a stage of preparation of nitrogenous compounds by the process according to the invention.

BACKGROUND

Fossil carbon-based resources (oil, coal, gas) cover 85% of the world's energy needs and serve as starting materials for 95% of organic chemical consumables (plastics, fertilizers, pesticides, and the like). The dwindling of oil resources and the accumulation of $CO_2$ resulting from their use thus present an ecological problem, an energy problem and a problem of availability of raw materials for the chemical industry. In this context, it is appropriate to provide novel routes for the synthesis of chemical consumables, so as to construct a lasting industry based on the use of renewable carbon-based resources.

To circumvent the petrochemical industry and to achieve the maximum recovery in value of its carbon-based waste, $CO_2$, in order to produce organic molecules, such as polymers, fertilizers, synthetic textiles, and the like, thus represents a key scientific challenge. This is because the recycling of $CO_2$ exhibits the twofold advantage of economizing on the fossil carbon-based resources (coal, hydrocarbons, and the like) normally used to synthesize organic molecules, while avoiding an increase in the emissions of this greenhouse gas.

However, the development of chemical reactions which make it possible to convert $CO_2$, in particular by replacing all the C—O bonds of the $CO_2$ with new C—H, C—C, C—N and C—S bonds, and the like, presents technical difficulties.

This is because, in view of the high thermodynamic stability of carbon dioxide, its conversion requires an external energy source so as to favor the thermodynamic balance of the chemical conversion and the use of catalyst to accelerate the reactions.

While $CO_2$ is often proposed as carbon source for its recovery in value as intermediates in chemistry (Sakakura, T., Choi, J. C. and Yasuda, H., *Chem. Rev.*, 2007, 107, 2365), the only reaction during which all the C—O bonds are split and new bonds are formed is the reduction of $CO_2$ to give methane (A. J. Morris, G. J. Meyer and E. Fujita, *Acc. Chem. Res.*, 2009, 42, 1983; A. Berkefeld, W. E. Piers and M. Parvez, *J. Am. Chem. Soc.*, 2010, 132, 10660). All the other known processes result in molecules always exhibiting C—O and/or C=O bonds, resulting from $CO_2$, with a partial reconstruction of the valency of the carbon (as in methanol, urea, formamides, and the like).

Mention may be made, as an example of conversion of $CO_2$ into novel chemical consumables by using a reactive chemical partner (high energy) to promote the thermodynamic balance of the chemical conversion of $CO_2$, of the industrial synthesis of urea obtained by condensation of ammonia with $CO_2$ (Sakakura, T., Choi, J. C. and Yasuda, H., *Chem. Rev.*, 2007, 107, 2365). This synthesis is shown in equation 1 below.

(equation 1)

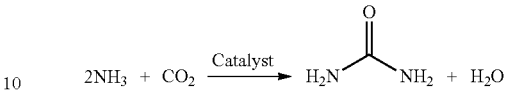

According to the same principle, the synthesis of polycarbonates by $CO_2$/epoxides copolymerization is in the process of industrialization as shown in equation 2 below (Panorama des voies de valorisation du $CO_2$ [Overview of the routes for recovering $CO_2$ in value], ADEME, June 2010, http://www2.ademe.fr/servlet/getDoc?cid=96&m=3&id=72052&p1=30&ref=12441).

(equation 2)

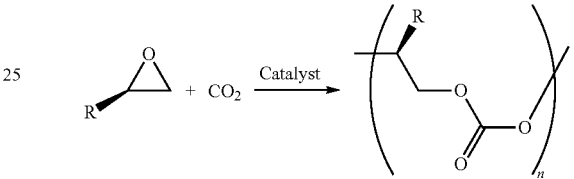

In both these syntheses (equations 1 and 2), there is no formal reduction of the central carbon atom of the $CO_2$. A C=O bond of each $CO_2$ converted is retained in the final structure.

Still with the aim of obtaining novel chemical consumables, the strategy envisaged can consist in completely modifying the coordination sphere of the $CO_2$ by replacing all the C—O bonds of the $CO_2$ with novel bonds of the C—N, C—H, C—C, C—S and/or C—O type.

To date, the reduction of the $CO_2$ to methane is the only catalytic process known for converting $CO_2$ into a molecule in which the four C—O bonds of the $CO_2$ have been replaced by four C—H bonds.

This strategy can also be applied in order to convert $CO_2$ into nitrogenous compounds chosen, for example, from amidines, nitrogenous heterocycles, and the like, which are a class of important chemical compounds in the chemical industry, where they are commonly used as reactants, medicaments, pesticides, herbicides, antifungals, and the like.

Among the amidines, the formamidines of general formula $R^1NCHNR^5R^6$ are generally synthesized by condensation of primary amines with formamides in the presence of a strong dehydrating agent, such as thionyl chloride ($SOCl_2$), trichlorophosphate or trifluoroacetic anhydride (M. Gall, J. M. McCall, R. E. TenBrink, P. F. Von Voigtlander and J. S. Mohrland, *Journal of Medicinal Chemistry*, 1988, 31, 1816-1820; S. Enthaler, K. Schröder, S. Inoue, B. Eckhardt, K. Junge, M. Beller and M. Drieβ, *European Journal of Organic Chemistry*, 2010, #25, pp. 4893-4901; K.-M. Cheng, Y.-Y. Huang, J.-J. Huang, K. Kaneko, M. Kimura, H. Takayama, S.-H. Juang and F. F. Wong, *Bioorganic and Medicinal Chemistry Letters*, 2010, vol. 20, #22, pp. 6781-6784; A. Mekhalfia, R. Mutter, W. Heal and B. Chen, *Tetrahedron*, 2006, vol. 62, #24, pp. 5617-5625). These synthetic routes generally require moderate heating (60° C.) to strong heating (180° C.) and require the use of toxic reactants ($SOCl_2$, $POCl_3$, and the like).

An alternative route is based on the synthesis of formamidines by reaction between a primary amine and a trialkyl orthoformate which is generally $(EtO)_3CH$ or $(MeO)_3CH$ (Samad Khaksar, Seyed Mohammad Vandat, Akbar Heydari and Mahmood Tajbakhsh, *Journal of Fluorine Chemistry*, 2010, vol. 131, No. 12, pp. 1377-1381). Applied to diamines, this reaction is used for the synthesis of nitrogenous heterocycles, such as benzimidazoles, quinazolinones, 3,4-dihydroquinazolines, and the like.

In order to use $CO_2$ as carbon source for synthesizing nitrogenous chemical compounds chosen, for example, from amidines, nitrogenous heterocycles, and the like, in which all the C—O bonds of the starting $CO_2$ are replaced with novel bonds of the C—N, C—H and/or C—O type, it is necessary to overcome a technical challenge which consists in combining the functionalization of the $CO_2$ with a stage of chemical reduction and a stage of deoxygenation. In order to maximize the energy yield of such a conversion, it is necessary to develop reactions with a limited number of stages (ideally just one) and which are catalyzed, in order to avoid energy losses of a kinetic nature.

SUMMARY

There thus exists a real need for a process for preparing nitrogenous compounds chosen, for example, from amidines, nitrogenous heterocycles, and the like, by conversion of $CO_2$, in particular by replacing all the C—O bonds of the starting $CO_2$ with new bonds of the C—N, C—H and/or C—O type, which overcomes the disadvantages of the prior art, said process making it possible to couple the functionalization of the carbon dioxide with a stage of chemical reduction and with a stage of deoxygenation.

In particular, there exists a real need for a process which makes it possible to obtain, in just one stage and with a very good selectivity, nitrogenous compounds from $CO_2$ and amines, under catalytic conditions, in the presence of a compound which provides for the reduction of the $CO_2$ and of a compound which provides for the functionalization of the $CO_2$.

Furthermore, the labeled nitrogenous compounds chosen, for example, from labeled amidines, labeled nitrogenous heterocycles, and the like, incorporating radioisotopes and/or stable isotopes, are of particular interest in many fields, such as, for example, in life sciences (study/elucidation of enzymatic mechanisms or of biosynthetic mechanisms, in biochemistry, and the like), environmental sciences (tracing of waste, and the like), research (study/elucidation of reaction mechanisms) or the research and development of novel pharmaceutical and therapeutic products. Thus, to develop a synthesis for the preparation of labeled nitrogenous compounds meeting the requirements indicated above may meet a real need.

There thus exists a real need to have available a process which makes it possible to obtain, in just one step and with a very good selectivity, the labeled nitrogenous compounds chosen, for example, from labeled amidines, labeled nitrogenous heterocycles, and the like, incorporating radioisotopes and/or stable isotopes, from the $CO_2$ and amines, under catalytic conditions, in the presence of a compound which provides for the reduction of the $CO_2$ and of a compound which provides for the functionalization of the $CO_2$, at least one of the reaction partners chosen from $CO_2$, the amines, the compound providing for the reduction of the $CO_2$ and the compound providing for the functionalization of the $CO_2$ being labeled.

It is a specific aim of the present invention to meet these needs by providing a process for the preparation of nitrogenous compounds of formula (I):

in which:

$R^1$ represents a hydrogen atom, an alkyl group, an alkenyl group, an alkynyl group, an aryl group, a heteroaryl group, a heterocycle, a carbonyl (—CO—) group, a silyl group, a siloxy group or an amino group, said alkyl, alkenyl, alkynyl, aryl, heteroaryl, heterocycle, silyl, siloxy and amino groups being optionally substituted, $R^1$ optionally comprises an H, C, N, O, F, Si and/or S as defined below;

H represents a hydrogen atom ($^1H$), deuterium ($^2H$) or tritium ($^3H$);

C represents a carbon atom ($^{12}C$) or a $^{11}C$, $^{13}C$, or $^{14}C$ isotope;

N represents a nitrogen atom ($^{14}N$) or a $^{15}N$ isotope;

O represents an oxygen atom ($^{16}O$) or an $^{18}O$ isotope;

F represents a fluorine atom ($^{19}F$) or a $^{18}F$ isotope;

Si represents a silicon atom ($^{28}Si$) or a $^{29}Si$ or $^{30}Si$ isotope;

S represents a sulfur atom ($^{32}S$), or a $^{33}S$, $^{34}S$ or $^{36}S$ isotope;

E represents an $R^5R^6N$— or $R^7O$— group with $R^5$, $R^6$ and $R^7$ representing, independently of one another, a hydrogen atom, an alkyl group, an alkenyl group, an alkynyl group, an aryl group, a heteroaryl group, a heterocycle, a (—(CO)—) group, a silyl group, a siloxy group or an amino group, said alkyl, alkenyl, alkynyl, aryl, heteroaryl, heterocycle, silyl, siloxy and amino groups being optionally substituted, or $R^5$ and $R^6$, taken together with the nitrogen atom to which they are bonded, form an optionally substituted heterocycle, or $R^1$ and $R^5$, taken together with the two nitrogen atoms to which they are respectively bonded, form an optionally substituted heterocycle, or $R^1$ and $R^7$, taken together with the nitrogen atom and oxygen atom to which they are respectively bonded, form an optionally substituted heterocycle, $R^5$, $R^6$ and $R^7$ optionally comprise an H, C, N, O, F, Si and/or S as defined above, $R^1$, N and O being as defined above;

characterized in that an amine of formula (II):

in which R¹ and N are as defined above, is reacted with CO₂, in which C and O are as defined above, in the presence:
of a catalyst,
of a silane compound of formula (III):

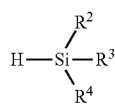
(III)

in which:
H is as defined above,
R², R³ and R⁴ represent, independently of one another, a hydrogen atom, a halogen atom, a hydroxyl group, an alkyl group, an alkenyl group, an alkynyl group, an alkoxy group, a silyl group, a siloxy group, an aryl group or an amino group, said alkyl, alkenyl, alkynyl, alkoxy, silyl, siloxy, aryl and amino groups being optionally substituted, or
R⁴ is as defined above and R² and R³, taken together with the silicon atom to which they are bonded, form an optionally substituted silylated heterocycle, and of a nucleophilic agent of formula (IV):
in which E is as defined above and H is a hydrogen atom.

The process of the invention has the advantage of making it possible to convert optionally labeled CO₂ into optionally labeled nitrogenous compounds with a large choice of optionally labeled amines of formula (II) (primary, secondary, aromatic, aliphatic, unsaturated, and the like, amines). In this process, the amines of formula (II) and the nucleophilic agent of formula (IV) serve essentially to functionalize the CO₂, and the silane compounds of formula (III) provide for the reduction of CO₂, under catalytic conditions.

The process of the invention makes it possible to replace, in just one stage, the two oxygen atoms of the CO₂ with hydrogen, nitrogen and/or oxygen atoms originating from the other reactants (or reaction partners) and to result in nitrogenous compounds of formula (I) with a good yield (yield which can range up to 100%).

In the context of the present invention, the yield is calculated with respect to the amount of amine of formula (II) initially introduced, on the basis of the amount of nitrogenous compound of formula (I) isolated:

Yield=n(nitrogenous compound)/(n(nitrogenous compound)+n(amine)), n being the amount of material.

As indicated above, the process of the invention makes it possible to obtain the nitrogenous compounds of formula (I) in "just one step". In other words, in contrast to the processes in which the starting amines are subjected to successive chemical reactions with successive addition (one at a time) of the other reactants, with or without separation of the intermediate products, the process of the invention takes place in "just one step" during which all of the reactants are found simultaneously in the reaction medium. Thus, industrially, the process of the invention is a great advantage as it makes it possible to gain in time, in production costs and in overall yield.

DETAILED DESCRIPTION

In the context of the present invention, the nitrogenous compounds of formula (I) obtained by the process of the invention can be any compound comprising an —N═CH—N or —N═CH—O unit which is acyclic or mono- or polycyclic and which optionally comprises one or more unsaturations (double or triple bond) in addition to the carbon-nitrogen double bond of the —N═CH—N or —N═CH—O unit, it being possible for said compound to be optionally substituted. Mention may be made, as examples of nitrogenous compounds of formula (I), of formamidine compounds and nitrogenous heterocycles chosen from benzimidazoles, benzoxazoles, quinazolinones or 3,4-dihydroquinazolines, for example.

Formamidine is understood to mean a class of cyclic or acyclic organic compounds comprising an —N═CH—N unit. Formamidines are formamide homologs in which the C═O bond is replaced by a C═N and are a subclass of amidines of formula —N═CR—N for which R is a hydrogen atom.

Within the meaning of the invention, nitrogenous heterocycles denote a mono- or polycyclic substituent comprising from 5 to 20 members, including at least two carbon atoms and at least one nitrogen atom and optionally at least one other heteroatom chosen from oxygen or sulfur. Nitrogenous heterocycles can comprise a carbon-nitrogen double bond (N═C) and can also comprise one or more other unsaturations. They can also be aromatic. Mention may be made, as nitrogenous heterocycles, of imidazoles, benzimidazoles, triazoles, oxazoles, benzoxazoles, pyrimidines, triazines, quinazolines, 3,4-dihydroquinazolines, quinazolinones or diazines. The nitrogenous heterocycle can optionally be substituted by one or more hydroxyl groups, one or more alkoxy groups, one or more siloxy groups, one or more thiol groups, one or more halogen atoms chosen from fluorine, chlorine, bromine and iodine atoms, one or more amino groups, one or more amido groups, one or more nitro (—NO₂) groups, one or more nitrile (—CN) groups, one or more aryl groups, or one or more alkyl groups, with the alkyl, alkoxy, thiol, aryl, amido and amino groups as defined in the context of the present invention.

"Alkyl" is understood to mean, within the meaning of the present invention, an optionally substituted, saturated or unsaturated and linear, branched or cyclic carbon-based radical comprising from 1 to 12 carbon atoms. Mention may be made, as saturated and linear or branched alkyl, for example, of the methyl, ethyl, propyl, butyl, pentyl, hexyl, heptyl, octyl, nonyl, decyl, undecyl and dodecanyl radicals and their branched isomers. Mention may be made, as cyclic alkyl, of the cyclopropyl, cyclobutyl, cyclopentyl, cyclohexyl, bicyclo [2.1.1]hexyl and bicyclo[2.2.1]heptyl radicals. Mention may be made, as unsaturated cyclic alkyls, for example, of cyclopentenyl or cyclohexenyl. The unsaturated alkyls, also known as "alkenyl" or "alkynyl", respectively comprise at least one double bond or one triple bond. Mention may be made, as such, for example, of the ethenyl, propenyl, butenyl, pentenyl, hexenyl, acetylenyl, propynyl, butynyl, pentynyl and hexynyl radicals and their branched isomers. The alkyl group, within the meaning of the invention including the alkenyl and alkynyl groups, can optionally be substituted by one or more hydroxyl groups, one or more alkoxy groups, one or more thiol groups, one or more halogen atoms chosen from the fluorine, chlorine, bromine and iodine atoms, one or more amino groups, one or more amido groups, one or more nitro (—NO₂) groups, one or more nitrile (—CN) groups, or one or more aryl groups, with the alkoxy, thiol, aryl, amino and amido groups as defined in the context of the present invention.

The term "aryl" denotes generally an aromatic cyclic substituent comprising from 6 to 20 carbon atoms. In the context of the invention, the aryl group can be mono- or polycyclic.

Mention may be made, by way of indication, of the phenyl, benzyl, naphthyl, phenanthrenyl and anthracenyl groups. The aryl group can optionally be substituted by one or more hydroxyl groups, one or more alkoxy groups, one or more thiol groups, one or more halogen atoms chosen from the fluorine, chlorine, bromine and iodine atoms, one or more amino groups, one or more amido groups, one or more nitro (—NO$_2$) groups, one or more nitrile (—CN) groups, one or more alkyl groups, or one or more aryl groups, with the alkoxy, thiol, alkyl, aryl, amido and amino groups as defined in the context of the present invention.

The term "heteroaryl" denotes generally an aromatic mono- or polycyclic substituent comprising from 5 to 20 members, including at least 2 carbon atoms, and at least one heteroatom chosen from nitrogen, oxygen or sulfur. The heteroaryl group can be mono- or polycyclic. Mention may be made, by way of indication, of the furyl, benzofuranyl, naphthofuranyl, benzopyranyl, pyrrolyl, indolyl, isoindolyl, azaindolyl, thiophenyl, benzothiophenyl, pyridyl, quinolinyl, isoquinolyl, imidazolyl, benzimidazolyl, triazolyl, pyrazolyl, oxazolyl, isoxazolyl, benzoxazolyl, thiazolyl, benzothiazolyl, isothiazolyl, diazinyl, pyridazinyl, pyrimidinyl, pyrazinyl, triazinyl, cinnolinyl, phthalazinyl, quinazolinyl, 1,1-diphenylhydrazinyl and 1,2-diphenylhydrazinyl groups. The heteroaryl group can optionally be substituted by one or more hydroxyl groups; one or more alkoxy groups; one or more thiol groups; one or more halogen atoms chosen from the fluorine, chlorine, bromine and iodine atoms; one or more amino groups; one or more amido groups; one or more nitro (—NO$_2$) groups; one or more nitrile (—CN) groups; one or more aryl groups; or one or more alkyl groups; with the alkyl, alkoxy, thiol, aryl, amido and amino groups as defined in the context of the present invention.

The term "alkoxy" means an alkyl group, as defined above, bonded via an oxygen atom (—O-alkyl).

The term "heterocycle" denotes generally a saturated or unsaturated and mono- or polycyclic substituent comprising from 5 to 20 members and comprising from 1 to 4 heteroatoms chosen, independently of one another, from nitrogen, oxygen and sulfur. Mention may be made, by way of indication, of the morpholinyl, piperidinyl, piperazinyl, pyrrolidinyl, imidazolyl, imidazolidinyl, imidazolinyl, pyrazolidinyl, tetrahydrofuranyl, tetrahydropyranyl, tetrahydropyrimidinyl, triazolyl, pyrazolyl, thianyl, oxazolidinyl, isoxazolidinyl, thiazolidinyl and isothiazolidinyl substituents. The heterocycle can optionally be substituted by one or more hydroxyl groups, one or more alkoxy groups, one or more thiol groups, one or more aryl groups, one or more halogen atoms chosen from the fluorine, chlorine, bromine and iodine atoms, one or more amino groups, one or more amido groups, one or more nitro (—NO$_2$) groups, one or more nitrile (—CN) groups, or one or more alkyl groups, with the alkyl, alkoxy, thiol, aryl, amido and amino groups as defined in the context of the present invention.

Halogen atom is understood to mean an atom chosen from the fluorine, chlorine, bromine or iodine atoms.

"Silyl" group is understood to mean a group of formula [—Si(X)$_3$] in which each X, independently of one another, is chosen from a hydrogen atom, one or more halogen atoms chosen from the fluorine, chlorine, bromine or iodine atoms, one or more alkyl groups, one or more alkoxy groups, one or more aryl groups, one or more siloxy groups, one or more amino groups, or one or more amido groups, with the alkyl, alkoxy, aryl, amido, amino and siloxy groups as defined in the context of the present invention. When at least one of the X symbols represents several siloxy groups, said siloxy groups can be repeated several times so as to result in polymeric organosilanes of general formula:

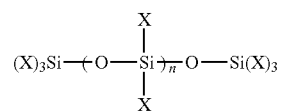

in which X is as defined above and n is an integer of between 1 and 20 000, advantageously 1000 and 5000. Mention may be made, as such, for example, of polydimethylsiloxane (PDMS) or polymethylhydrosiloxane (PMHS).

"Siloxy" group is understood to mean a silyl group as defined above bonded via an oxygen atom (—O—Si(X)$_3$).

Within the meaning of the invention, "silylated heterocycle" is understood to mean a saturated or unsaturated and mono- or polycyclic substituent comprising from 5 to 15 members and comprising at least one silicon atom and optionally at least one other heteroatom chosen from nitrogen, oxygen or sulfur. Said silylated heterocycle can optionally be substituted by one or more hydroxyl groups, one or more alkyl groups, one or more alkoxy groups, one or more thiol groups, one or more halogen atoms chosen from the fluorine, chlorine, bromine and iodine atoms, one or more aryl groups, one or more amino groups, or one or more amido groups, with the alkyl, alkoxy, thiol, aryl, amino and amido groups as defined in the context of the present invention. Mention may be made, among silylated heterocycles, for example, of 1-silacyclo-3-pentene or 1-methyl-1-hydrido-2,3,4,5-tetraphenyl-1-silacyclo-pentadiene, according to the formulae below.

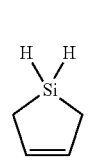 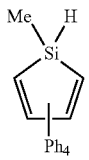

1-silacyclo-3-pentene    1-methyl-1-hydrido-2,3,4,5-tetraphenyl-1-silacyclopentadiene Mention may also be made, for example, of methylsiloxane, 1-phenyl-1-silacyclohexane, 1-sila-bicyclo[2.2.1]heptane, 1-methyl-1-silacyclopentane and 9,9-dihydro-9-silafluorene, corresponding to the formulae below.

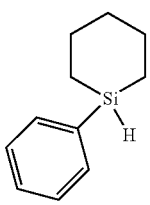 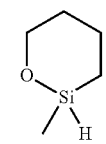

1-phenyl-1-silacyclohexane    methylsiloxane

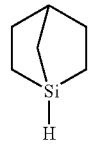 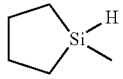

1-silabicyclo[2.2.1]heptane    1-methyl-1-silacyclopentane

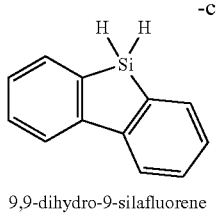

9,9-dihydro-9-silafluorene

The silylated heterocycles of the invention can be available commercially or can if appropriate be prepared by the known synthetic processes, such as, for example, described by C. L. Smith et al., *Journal of Organometallic Chemistry*, 81 (1974), pp. 33-40; G. D. Homer, *Journal of the American Chemical Society*, 95, 23, (1973), pp. 7700-7707; L. Spialter et al., *Journal of the American Chemical Society*, 93, 22 (1971), pp. 5682-5686; R. West, *Journal of the American Chemical Society* (1954), pp. 6015-6017. A person skilled in the art will be in a position to employ and adapt the known processes to the synthesis of the various silylated heterocycles.

"Amino" group is understood to mean a group of formula —NR$^8$R$^9$ in which:

R$^8$ and R$^9$ represent, independently of one another, a hydrogen atom, an alkyl group, an alkenyl group, an alkynyl group, an aryl group, a heteroaryl group, a heterocycle, a —CO—R$^{10}$ group, a silyl group or a siloxy group, with the alkyl, alkenyl, alkynyl, aryl, heteroaryl, heterocycle, silyl and siloxy groups as defined in the context of the present invention, or R$^8$ and R$^9$, taken together with the nitrogen atom to which they are bonded, form a heterocycle optionally substituted by one or more hydroxyl groups, one or more alkyl groups, one or more alkoxy groups, one or more halogen atoms chosen from the fluorine, chlorine, bromine and iodine atoms, one or more amino groups, one or more nitro (—NO$_2$) groups, one or more nitrile (—CN) groups, or one or more aryl groups, with the alkyl, alkoxy, aryl and amino groups as defined in the context of the present invention; and R$^{10}$ represents a hydrogen atom, an alkyl group, an alkenyl group, an alkynyl group, an aryl group, a heteroaryl group, a heterocycle, a silyl group or a siloxy group, with the alkyl, alkenyl, alkynyl, aryl, heteroaryl, heterocycle, silyl and siloxy groups as defined in the context of the present invention.

"Amido" group is understood to mean a group of formula —CO—NR$^8$R$^9$, in which:

R$^8$ and R$^9$ represent, independently of one another, a hydrogen atom, an alkyl group, an alkenyl group, an alkynyl group, an aryl group, a heteroaryl group, a heterocycle, a —CO—R$^{10}$ group, a silyl group or a siloxy group, with the alkyl, alkenyl, alkynyl, aryl, heteroaryl, heterocycle, silyl and siloxy groups as defined in the context of the present invention, or R$^8$ and R$^9$, taken together with the nitrogen atom to which they are bonded, form a heterocycle optionally substituted by one or more hydroxyl groups, one or more alkyl groups, one or more alkoxy groups, one or more thiol groups, one or more halogen atoms chosen from the fluorine, chlorine, bromine and iodine atoms, one or more amino groups, one or more nitro (—NO$_2$) groups, one or more nitrile (—CN) groups, or one or more aryl groups, with the alkyl, alkoxy, thiol, aryl and amino groups as defined in the context of the present invention; and R$^{10}$ represents a hydrogen atom, an alkyl group, an alkenyl group, an alkynyl group, an aryl group, a heteroaryl group, a heterocycle, a silyl group or a siloxy group, with the alkyl, alkenyl, alkynyl, aryl, heteroaryl, heterocycle, silyl and siloxy groups as defined in the context of the present invention.

"Thiol" group is understood to mean a group of formula —SR$^{12}$, in which R$^{12}$ represents a hydrogen atom, an alkyl group, an alkenyl group, an alkynyl group, an aryl group, a heteroaryl group, a heterocycle, a silyl group or a siloxy group with the alkyl, alkenyl, alkynyl, aryl, heteroaryl, heterocycle, silyl and siloxy groups as defined in the context of the present invention.

The substituents, radicals and groups defined above can optionally comprise deuterium ($^2$H), tritium ($^3$H), $^{11}$C, $^{13}$C, $^{14}$C, $^{15}$N, $^{18}$O, $^{18}$F, $^{29}$Si, $^{30}$Si, $^{33}$S, $^{34}$S or $^{36}$S.

When the compounds of formula (I), (II), (III) and (IV) comprise at least one radioactive label/radioactive tracer or one isotope, they can also be denoted by the formulae (I'), (II'), (III') and (IV').

According to a preferred alternative form of the invention, in the amine of formula (II), R$^1$ represents a hydrogen atom, an alkyl group, an aryl group, a heteroaryl group, a heterocycle or an amino group, said alkyl, amino, aryl, heterocycle and heteroaryl groups optionally being substituted.

According to another preferred alternative form, in the amine of formula (II), R$^1$ represents a hydrogen atom, an alkyl group chosen from the methyl, ethyl, propyl, butyl, pentyl, hexyl or heptyl groups or their branched isomers or the cyclohexyl group, an aryl group chosen from benzyl, phenyl or naphthyl, or a heteroaryl group chosen from diazinyl, pyridazinyl, pyrimidinyl, pyrazinyl, imidazolyl or benzimidazolyl, said alkyl, aryl and heteroaryl groups optionally being substituted.

According to another preferred alternative form of the invention, in the silane compound of formula (III), R$^2$, R$^3$ and R$^4$ represent, independently of one another, a hydrogen atom, an alkyl group, an alkoxy group, an aryl group, a silyl group or a siloxy group, said alkyl, alkoxy, silyl, siloxy and aryl groups optionally being substituted.

Preferably, in the silane compound of formula (III), R$^2$, R$^3$ and R$^4$ represent, independently of one another:

a hydrogen atom;

an alkyl group chosen from methyl, ethyl, propyl, butyl, pentyl, hexyl or heptyl groups or their branched isomers;

an alkoxy group, the alkyl group of which is chosen from the methyl, ethyl, propyl, butyl, pentyl, hexyl or heptyl groups or their branched isomers;

an aryl group chosen from the benzyl or phenyl groups;

a silyl group of formula [—Si(X)$_3$] in which each X symbol, independently of one another, is chosen from a hydrogen atom, one or more halogen atoms chosen from the chlorine, bromine or iodine atoms, one or more alkyl groups chosen from the methyl, ethyl, propyl, butyl, pentyl, hexyl or heptyl groups or their branched isomers, one or more alkoxy groups, the alkyl group of which is chosen from the methyl, ethyl, propyl, butyl, pentyl, hexyl or heptyl groups or their branched isomers, one or more siloxy groups, the —Si(X)$_3$ group of which is as described in this embodiment, several siloxy groups which reoccur several times resulting in polymeric organosilanes of general formula:

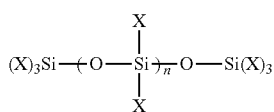

in which X is as defined in this embodiment and n is an integer of between 1 and 20 000, advantageously between 1000 and 5000.

As already indicated, just like the amine, the nucleophilic agent E-H of formula (IV) serves to functionalize the $CO_2$.

According to a preferred alternative form of the invention, E represents an $R^5R^6N$— group with $R^5$ and $R^6$ representing, independently of one another, a hydrogen atom, an alkyl group, an aryl group, a heteroaryl group, a heterocycle or an amino group, said alkyl, aryl, heteroaryl, heterocycle and amino groups optionally being substituted, or $R^5$ and $R^6$, taken together with the nitrogen atom to which they are bonded, form an optionally substituted heterocycle.

Preferably, E represents an $R^5R^6N$— group with $R^5$ and $R^6$ representing, independently of one another, a hydrogen atom, an alkyl group chosen from the methyl, ethyl, propyl, butyl, pentyl, hexyl or heptyl groups or their branched isomers or a cyclohexyl group, an aryl group chosen from benzyl, phenyl or naphthyl, or a heteroaryl group chosen from diazinyl, pyridazinyl, pyrimidinyl, pyrazinyl, imidazolyl or benzimidazolyl, said alkyl, aryl and heteroaryl groups optionally being substituted.

The amine of formula (II) and the nucleophilic agent of formula (IV) are two distinct compounds which may or may not be identical according to whether it is desired to obtain a symmetrical or asymmetrical nitrogenous compound. According to a particularly preferred alternative form, the nucleophilic agent E-H of formula (IV) and the amine of formula (II) are identical.

Catalyst, within the meaning of the invention, is understood to mean any compound which is capable of modifying, in particular by increasing, the rate of the chemical reaction in which it participates and which is regenerated at the end of the reaction. This definition encompasses both catalysts, that is to say compounds which exert their catalytic activity without having to be subjected to any modification or conversion, and compounds (also known as precatalysts) which are introduced into the reaction medium and which are converted therein into a catalyst.

The catalysts can be chosen from organic catalysts or metal catalysts chosen from metal salts or complexes. Organic catalysts exhibit the advantage of making it possible to escape the problems of toxicity generally observed for metal catalysts and also the problems of costs associated with the use of precious metals. In the process of the invention, the catalyst is preferably organic.

The organic catalysts are generally organic bases chosen from:

nitrogenous bases, such as, for example, secondary or tertiary amines chosen from triazabicyclodecene (TBD); N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt or N-diisopropylethylamine (DIPEA or DIEA);

phosphorus-based bases, such as, for example, alkyl- and arylphosphines chosen from triphenylphosphine, 2,2'-bis(diphenylphosphino)-1,1'-binaphthyl (BINAP) or triisopropylphosphine; alkyl- and arylphosphonates chosen from diphenyl phosphate, triphenyl phosphate (TPP), tri(isopropylphenyl)phosphate (TIPP), cresyl diphenyl phosphate (CDP) or tricresyl phosphate (TCP); or alkyl and aryl phosphates chosen from di(n-butyl) phosphate (DBP), tris(2-ethylhexyl)phosphate or triethyl phosphate;

carbon-based bases for which the protonation takes place on a carbon atom, such as, for example, an N-heterocyclic carbene, such as a carbene resulting from an imidazolium salt chosen from 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di(tert-butyl)-1H-imidazol-3-ium (carbene F) or 1,3-di(tert-butyl)-4,5-dihydro-1H-imidazol-3-ium salts, said salts being, for example, in the form of chloride salts, as represented below:

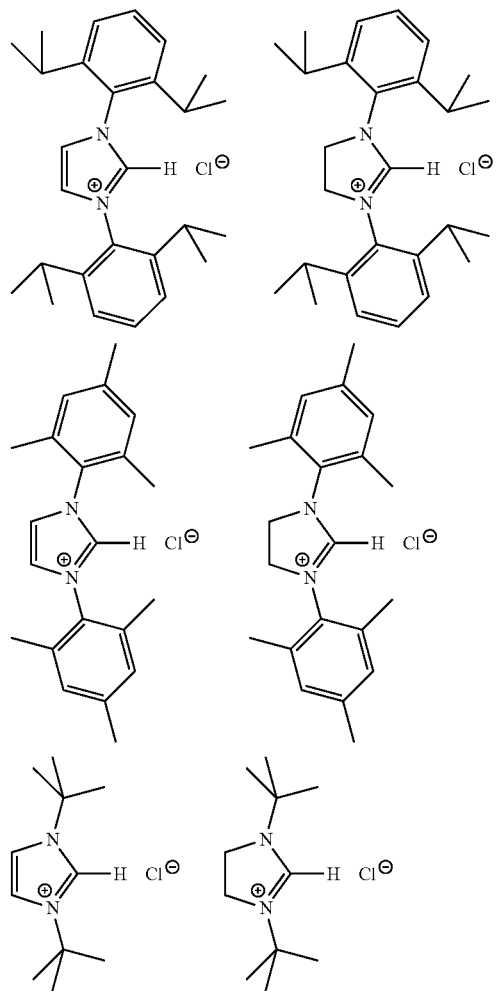

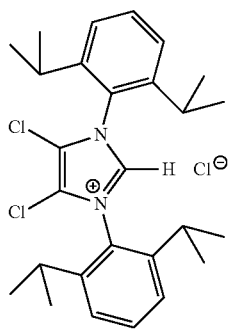

or oxygen-based bases, such as, for example, hydrogen peroxide, benzoyl peroxide or an alkoxide chosen from sodium or potassium methoxide, ethoxide, propoxide, butoxide, pentoxide or hexoxide.

The organic catalyst is advantageously:

a secondary or tertiary amine chosen from triazabicyclodecene (TBD), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt or N-diisopropylethylamine (DIPEA or DIEA), or an N-heterocyclic carbene, such as a carbene resulting from an imidazolium salt chosen from 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di(tert-butyl)-1H-imidazol-3-ium (carbene F) or 1,3-di(tert-butyl)-4,5-dihydro-1H-imidazol-3-ium salts, said salts being, for example, in the form of chloride salts, as represented below:

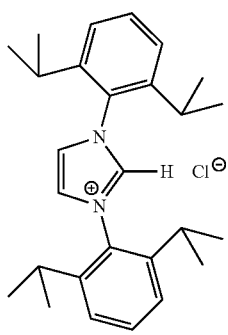 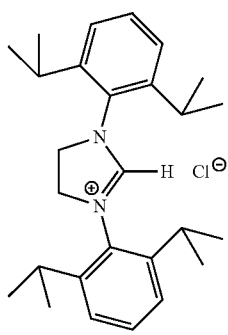

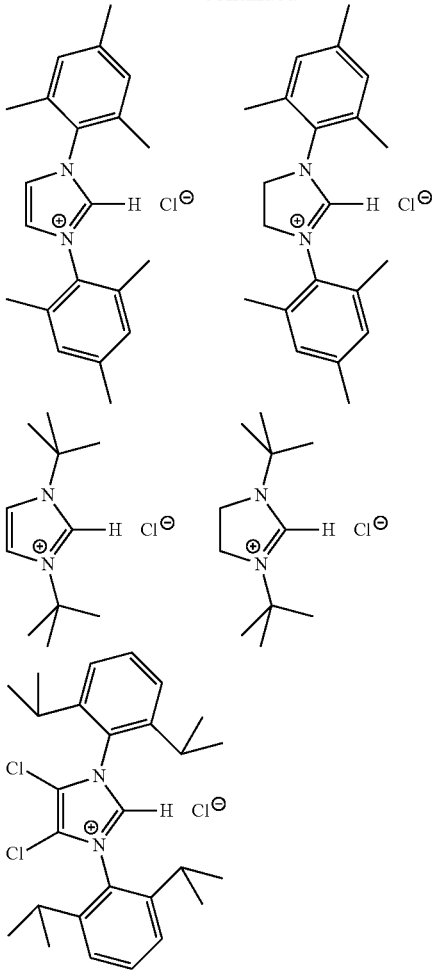

According to a preferred alternative form of the invention, the organic catalyst is chosen from triazabicyclodecene (TBD), N-methyltriazabicyclodecene (MeTBD), 1,8-diazabicyclo[5.4.0]undec-7-ene (DBU), or an N-heterocyclic carbene, such as a carbene resulting from an imidazolium salt, such as 1,3-bis(2,6-diisopropylphenyl)-1H-imidazol-3-ium chloride (carbene A), 1,3-bis(2,6-diisopropylphenyl)-4,5-dihydro-1H-imidazol-3-ium chloride (carbene C), 1,3-di(tert-butyl)-1H-imidazol-3-ium chloride, 1,3-di(tert-butyl)-4,5-dihydro-1H-imidazol-3-ium chloride (carbene F), 1,3-bis(2,4,6-trimethylphenyl)-1H-imidazol-3-ium chloride (carbene B), 1,3-bis(2,4,6-trimethylphenyl)-4,5-dihydro-1H-imidazol-3-ium chloride (carbene D) or 4,5-dichloro-1,3-bis(2,6-diisopropylphenyl)-1H-imidazol-3-ium chloride (carbene E).

When the catalyst is a metal catalyst, it can be chosen from the salts or complexes of:

metals chosen from boron, silicon, aluminum, gallium, tin or indium;
alkali metals chosen from sodium or potassium;
alkaline earth metals chosen from magnesium or calcium;
transition metals chosen from nickel, iron, cobalt, zinc, copper, rhodium, ruthenium, platinum, palladium or iridium;
rare earth metals chosen from lanthanum, cerium, praseodymium or neodymium.

By way of examples, the metal catalyst can be chosen from the following salts or complexes:

Al(OiPr)$_3$, SnCl$_2$ or InBr$_3$, as metal salts or complexes;

Na$_2$CO$_3$, K$_2$CO$_3$ or Cs$_2$CO$_3$, as salts or complexes of alkali metals;

MgSO$_4$ or Ca(BH$_4$)$_2$, as salts or complexes of alkaline earth metals;

Fe(BH$_4$)$_2$.6H$_2$O, Fe(BF$_4$)$_2$. 6H$_2$O, Fe(acac)$_3$, CuCl, Cu(OAc)$_2$(H$_2$O), Zn(OAc)$_2$, Zn(BDI)Et, ZnEt$_2$, ZnCl$_2$ or ZnSO$_4$, as salts or complexes of transition metals;

La(OTf)$_3$ or CeCl$_3$, as salts or complexes of rare earth metals.

Metal complex is understood to mean an organometallic or inorganic coordination compound in which a metal ion is bonded to an organic or inorganic ligand. An organometallic or inorganic complex can be obtained by mixing a metal salt with a ligand, the latter bonding to the metal via phosphorus, carbon, nitrogen, oxygen, hydrogen or silicon atoms, for example. Mention may be made, as organic or inorganic ligand, for example, of phosphines (PRR'R"), amines (NRR'R"), ethers (R—O—R'), carbenes, thiols (R—S—H), amidines, guanidines ((RR' N)(R$^a$R$^b$N)C=N—R"), with R, R', R", R$^a$ and Rb representing, independently of one another, a hydrogen atom, an alkyl group, an aryl group, a heteroaryl group or a heterocycle, with the alkyl, aryl, heteroaryl and heterocycle groups as defined in the context of the present invention. Mention may be made, as examples of ligands, of tris[2-(diphenylphosphino)ethyl]phosphine (PP$_3$), carbene A or tricyclohexylphosphine.

The catalysts can, if appropriate, be immobilized on heterogeneous supports in order to ensure ready separation of said catalyst and/or the recycling thereof. Said heterogeneous supports can be chosen from supports based on silica gel or on plastic polymers, such as, for example, polystyrene, carbon-based supports chosen from carbon nanotubes, silicon carbide, alumina or magnesium chloride (MgCl$_2$).

In the process according to the invention, the reaction can be carried out under a CO$_2$ pressure by spurging CO$_2$ into the reaction medium or under a dry atmosphere comprising CO$_2$ (dried ambient air comprising, for example, approximately 78% by volume of nitrogen, 21% by volume of oxygen and approximately from 0.2% to 0.04% by volume of carbon dioxide). The reaction can also be carried out using supercritical CO$_2$.

Preferably, the reaction is carried out under a CO$_2$ pressure.

The pressure of the CO$_2$ can then be between 1 and 50 bar, preferably between 1 and 30 bar, more preferably between 1 and 10 bar, limits included.

The temperature of the reaction can be between 25 and 150° C., preferably between 50 and 125° C. and more preferably between 70 and 100° C., limits included.

The duration of the reaction depends on the degree of conversion of the amine of formula (II). The reaction is advantageously maintained until complete conversion of the amine of formula (II). The reaction is carried out for a period of time of 5 minutes to 72 hours, advantageously of 15 minutes to 48 hours and preferably of 1 to 48 hours, limits included.

The process of the invention, in particular the reaction between the different reactants, can take place in a or a mixture of at least two solvent(s) chosen from:

ethers, preferably diethyl ether or THF;

hydrocarbons, preferably benzene or toluene;

nitrogenous solvents, preferably pyridine or acetonitrile;

sulfoxides, preferably dimethyl sulfoxide;

alkyl halides, preferably chloroform or methylene chloride.

According to a preferred alternative form of the invention, it is not necessary to add an additional solvent. In this case, the amine of formula (II) is the solvent. Thus, in addition to its role of functionalizing the CO$_2$, the amine serves as solvent.

The molar ratio of the silane compound of formula (III) to the amine of formula (II) is from 1 to 10 and preferably from 1 to 3, limits included.

The amount of catalyst is from 0.001 to 1 molar equivalent, preferably from 0.01 to 1 molar equivalent, more preferably from 0.01 to 0.9 molar equivalent and more preferably still from 0.01 to 0.5 molar equivalent, limits included, with respect to the amine of formula (II).

The different reactants used in the process of the invention (the amines of formula (II), the nucleophilic agents of formula (IV), the silane compounds of formula (III), the (pre) catalysts, and the like) are generally commercial compounds or can be prepared by any process known to a person skilled in the art.

As already indicated, the invention also relates to the process for the preparation of labeled nitrogenous compounds of formula (I'):

in which:

R$^1$* is as defined above for R$^1$ and optionally comprises an H*, C*, N*, O*, F, Si* and/or S* as defined below;

E* represents R$^5$*R$^6$—N*— or R$^7$*O*—, with

R$^5$*, R$^6$* and R$^7$* as defined above for R$^5$, R$^6$ and R$^7$,

O* representing an oxygen atom ($^{16}$O) or a $^{17}$O or $^{18}$O isotope, and N* representing a nitrogen atom ($^{14}$N) or a $^{15}$N isotope;

H* represents a hydrogen atom ($^1$H), deuterium ($^2$H) or tritium ($^3$H);

C* represents a carbon atom ($^{12}$V) or a $^{11}$C, $^{13}$C or $^{14}$C isotope;

N* represents a nitrogen atom ($^{14}$N) or a $^{15}$N isotope;

O* represents an oxygen atom ($^{16}$O) or an $^{18}$O isotope;

F* represents a fluorine atom ($^{19}$F) or a $^{18}$F isotope;

Si* represents a silicon atom ($^{28}$Si) or a $^{29}$Si or $^{30}$Si isotope;

S* represents a sulfur atom ($^{32}$S) or a $^{33}$S, $^{34}$S or $^{38}$S isotope;

characterized in that an amine of formula (II'):

in which R¹* and N* are as defined above, is reacted with C*O*₂, in which C* and O* are as defined above, in the presence:
of a catalyst:
of a silane compound of formula (III'):

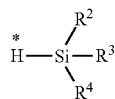
(III')

in which:
R², R³, R⁴ and H* are as defined above, and
of a nucleophilic agent of formula (IV'):

E*-H (IV')

in which E* is as defined above and H is a hydrogen atom.

The compounds of formula (I') correspond in fact to the compounds of formula (I) comprising at least one chosen radioactive label/radioactive tracer or one chosen isotope.

Isotopes are understood to mean, for one and the same element, two atoms having the same number of protons (and of electrons) but a different number of neutrons. As they have the same number of electrons and protons, the chemical properties of isotopes of one and the same element are virtually identical. However, there may exist slight variations in the rate of a chemical reaction when one of the atoms of a reactant is replaced by one of its isotopes. On the other hand, as the nucleus does not comprise the same number of neutrons, the mass of the atoms varies, which may render the atom unstable: this is why they may be radioactive. They are then radioactive isotopes. In the context of the invention, the term "isotopes" may also encompass "radioactive isotopes".

Radioactive labeling is the fact of combining, with a given molecule or a given compound, an isotope which will make it possible to monitor the change and/or the fixing of the molecules, for example, in an organ. The radioactive tracer is the radioactive element(s) present within a molecule for monitoring the course of this substance, for example, in an organ.

The process of the invention can be carried out with radioactive isotopes and/or stable isotopes carried by the different reactants as indicated above. It can thus make possible access to the nitrogenous compounds labeled with $^{11}C$, $^{13}C$, $^{14}C$, $^{15}N$, $^{2}H$ (D), $^{3}H$ (T), $^{17}O$ and/or $^{18}O$.

A direct application of the process can then be the synthesis of labeled formamidines or labeled nitrogenous heterocycles, such as benzimidazoles, benzoxazoles, quinazolinones, 3,4-dihydroquinazolines, and the like, incorporating radioactive isotopes and/or stable isotopes using labeled reactants. This method will thus make possible access to formamidines labeled with $^{11}C$, $^{13}C$, $^{14}O$, $^{15}N$, $^{2}H$ (D) and $^{3}H$ (T), $^{17}O$ and $^{18}O$, as shown in FIG. 1.

The use of molecules for tracing, metabolism, imaging, and the like, purposes is described in detail in the literature (U. Pleiss and R. Voges, "Synthesis and Applications of Isotopically Labelled Compounds", Volume 7, Wiley-VCH, 2001; R. Voges, J. R. Heys and T. Moenius, "Preparation of Compounds Labeled with Tritium and Carbon-14", Wiley-VCH, Chippenham (UK), 2009). The possibility of forming labeled formamide compounds can be provided by the availability of the corresponding labeled reactants, for example, by:
the amines R¹NH₂ enriched in $^{15}N$ are accessible from ammonium chloride enriched in $^{15}N$ [$^{15}NH_4$][Cl] (Yong-Joo Kim, Max P. Bernstein, Angela S. Galiano Roth, Floyd E. Romesberg, Paul G. Williard, David J. Fuller, Aidan T. Harrison and David B. Collum, J. Org. Chem., 1991, 56, pp. 4435-4439);
amines R¹NH₂ with R¹ labeled are prepared by the synthetic routes described in detail by U. Pleiss and R. Voges, "Synthesis and Applications of Isotopically Labelled Compounds", Volume 7, Wiley-VCH, 2001, and R. Voges, J. R. Heys and T. Moenius, "Preparation of Compounds Labeled with Tritium and Carbon-14", Wiley-VCH, Chippenham (UK), 2009;
CO₂ labeled with $^{11}C$ or $^{14}C$ is the main source of $^{11}C$ and $^{14}C$ is obtained by acidification of labeled barium carbonate Ba$^{14}$CO₃ (R. Voges, J. R. Heys and T. Moenius, "Preparation of Compounds Labeled with Tritium and Carbon-14", Wiley-VCH, Chippenham (UK), 2009);
CO₂ labeled with $^{17}O$ or $^{18}O$ is used in synthetic chemistry to produce molecules labeled with $^{17}O$ and $^{18}O$ (Christopher J. Dinsmore and Swati P. Mercer, Organic Letters, 2004, vol. 6, No. 17, 2885-2888; John T. Groves and Yoshihito Watanabe, J. Am. Chem. Soc., 1988, 110, pp. 8443-8452);
alcohols labeled with $^{17}O$ or $^{18}O$ are used in synthetic chemistry to produce molecules labeled with $^{17}O$ or $^{18}O$ (Christopher J. Dinsmore and Swati P. Mercer, Organic Letters, 2004, vol. 6, No. 17, 2885-2888; John T. Groves and Yoshihito Watanabet, J. Am. Chem. Soc., 1988, 110, 8443-8452);
silanes R³R⁴R⁵Si—H labeled with $^{2}H$ (deuterium or D) or $^{3}H$ (tritium or T) are accessible from the corresponding chlorosilane R³R⁴R⁵Si—Cl and lithium hydride (LiH) or lithium aluminum hydride (LiAlH₄), the hydrides both being available in deuterated and tritiated versions (T. A. Kochina, D. V. Vrazhnov, E. N. Sinotova, V. V. Avrorin, M. Yu. Katsap and Yu. V. Mykhov, Russian Journal of General Chemistry, Vol. 72, No. 8, 2002, pp. 1222-1224; E. A. Shishigin, V. V. Avrorin, T. A. Kochina and E. N. Sinotova, Russian Journal of General Chemistry, Vol. 75, No. 1, 2005, pp. 152).

While the labeling of nitrogenous compounds is possible with the $^{11}C$, $^{13}C$, $^{14}C$, $^{15}N$, $^{2}H$ (D), $^{3}H$ (T), $^{17}O$ and $^{18}O$ nuclei, the application aiming at the formation of molecules labeled with $^{14}C$ may be the most promising in terms of impact and demand.

Molecules labeled with $^{14}C$ have contributed to many advances in life sciences (enzymatic mechanisms, biosynthetic mechanisms, biochemistry), environmental sciences (tracing of waste), research (elucidation of reaction mechanisms) or diagnosis, or research and development of novel pharmaceutical and therapeutic products. This is because molecules labeled with $^{14}C$ exhibit an advantage in metabolical studies because $^{14}C$ is easily detectable and quantifiable in both an in vitro and in vivo environment.

The main source of $^{14}C$ is $^{14}CO_2$, which is obtained by acidification of barium carbonate Ba$^{14}$CO₃. The development of processes for the synthesis of base molecules used in the preparation of medicaments is thus essential in order to produce active principles labeled with $^{14}C$, the metabolism of which can thus be determined (R. Voges, J. R. Heys and T. Moenius, "Preparation of Compounds Labeled with Tritium and Carbon-14", Wiley-VCH, Chippenham (UK), 2009).

The major constraint limiting the synthesis of molecules labeled with $^{14}C$ is the need to have a high yield of $^{14}C$ product formed with respect to the amount of $^{14}CO_2$ used and to be based on a restricted number of steps in order to limit as much as possible the costs related to the use of Ba$^{14}$CO₃ (U. Pleiss and R. Voges, "Synthesis and Applications of Isotopically Labelled Compounds", Volume 7, Wiley-VCH, 2001;

R. Voges, J. R. Heys and T. Moenius, "Preparation of Compounds Labeled with Tritium and Carbon-14", Wiley-VCH, Chippenham (UK), 2009).

The process according to the invention meets these requirements as the $CO_2$ operating pressure can be low, for example from 0.2 to 1 bar. In addition, the degree of incorporation of $CO_2$ (or yield with respect to the $CO_2$ introduced) remains high and can, for example, exceed 95%.

The conditions of temperature, of reaction time and of solvent and also the amount of reactants and catalysts employed in the process for the preparation of labeled nitrogenous compounds of formula (I') are those described above in the context of the process for the preparation of nitrogenous compounds of formula (I).

Finally, the synthesis of nitrogenous compounds labeled with $^{14}C$ according to the process of the invention is a very marked improvement in comparison with the known technologies as it makes it possible to access the nitrogenous compounds in just one step starting from $CO_2$ with good yields and a good selectivity. The advantage of nitrogenous compounds labeled with $^{14}C$ in the synthesis of complex molecules labeled with $^{14}C$ is illustrated in the following references in the case of pharmaceutical active principles: J. Z. Ho et al., Helvetica Chimica Acta, 2005, 88, p. 1040; I. V. Ekhato and S. Bonacorsi Jr., J. Label. Compd. Radiopharm., 2011, 54, pp. 202-205; Kenneth K. Chan and James A. Staroscik, Journal of Medicinal Chemistry, 1977, vol. 20, No. 4, p. 598.

In this alternative form of the process according to the invention, when the reaction is carried out under a $CO_2$ pressure, the pressure of the $CO_2$ can then be between 0.2 and 50 bar, preferably between 0.2 and 30 bar and more preferably between 0.2 and 10 bar, limits included.

Another subject matter of the invention is the use of the process for the preparation of nitrogenous compounds of formula (I) according to the invention in the manufacture of vitamins, pharmaceutical products, adhesives, acrylic fibers, synthetic leather, pesticides, herbicides, antifungals and fertilizers.

An additional subject matter of the invention is a process for the manufacture of vitamins, pharmaceutical products, adhesives, acrylic fibers, synthetic leather, pesticides, herbicides, antifungals and fertilizers, characterized in that it comprises a step of preparation of nitrogenous compounds of formula (I) by the process according to the invention.

Another subject matter of the invention consists of a process for the manufacture of tracers and radioactive tracers, characterized in that it comprises a step of preparation of labeled nitrogenous compounds of formulae (I) and (I') by the process according to the invention.

As already indicated, the process according to the invention results in the formation of nitrogenous compounds, in just one step, with a good yield (ranging up to 100%). A simple filtration may make it possible to recover the optionally supported catalyst and to remove the possible silylated by-products formed.

Other advantages and characteristics of the present invention will become apparent on reading the examples below, given by way of illustration and without implied limitation, and the appended figures, in which:

FIG. 1 gives a diagrammatic representation of the synthesis of formamidines labeled with radioisotopes and/or stable isotopes ($^{11}C$, $^{13}C$, $^{14}C$, $^{15}N$, $^2H$ (D), $^3H$ (T), $^{17}O$ and/or $^{18}O$) with the process of the invention.

EXAMPLES

Example 1

The process for the preparation of nitrogenous compounds of formula (I) can be carried out according to the following experimental protocol.

The reactants used, in particular the amine $R^1NH_2$, the (pre)catalyst, the nucleophilic agent EH and the silane compound, are products sold by Sigma-Aldrich, Acros and Alfa Aesar.

The amine $R^1NH_2$ (1 molar equivalent), the (pre)catalyst (from 0.001 to 1 molar equivalent), the silane compound (1 equivalent) and the solvent are introduced into a Schlenk tube under an inert atmosphere in a glove box and the Schlenk tube is subsequently sealed with a J. Young tap. The concentration of amine and of silane compound in the reaction mixture is approximately 1M (concentration calculated on the basis of the volume of solvent introduced). The order of introduction of the reactants is not important.

The Schlenk tube is subsequently placed under $CO_2$ pressure (from 1 to 3 bar) using a vacuum line and is then heated at a temperature of between 25 and 100° C. until the complete conversion of the amine (reaction from 5 minutes to 72 hours).

Once the reaction is complete, the volatile compounds are removed under reduced pressure and the reaction mixture is purified by chromatography on silica gel. The use of THF as eluent makes it possible to recover the possible silylated by-products (mixture of siloxanes and silanols). In a second step, ethyl acetate is used as eluent in order to recover the nitrogenous compound. The ethyl acetate present in the solution thus collected is then removed under reduced pressure, so as to obtain the analytically pure nitrogenous compound.

A body of results is presented below, giving examples of conversions of amines into nitrogenous compounds (determined by NMR and/or GC/MS). The classes of products obtained depend on the nature of the nucleophilic agent used. The different classes are listed in the different tables below. The structures of the amines, of the nucleophilic agent, of the silanes and of the (pre)catalysts tested are represented on each occasion.

The general reaction scheme is as follows:

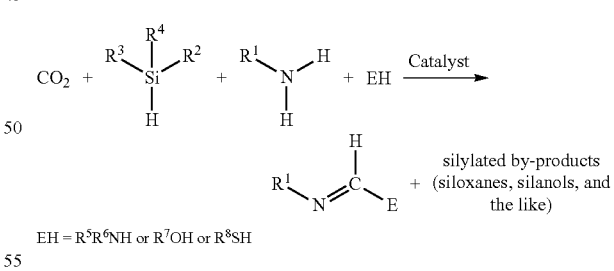

A—Synthesis of Benzimidazole and Derivatives from Aromatic 1,2-Diamines

The first results presented describe the synthesis of benzimidazole rings and derivatives from aromatic 1,2-diamines. In this case, the amine $R^1NH_2$ and the nitrogenous nucleophilic agent $R^5R^6NH$ are two reactive functional groups of one and the same molecule (diamine) and are thus connected via a covalent bond. This bond is preferably an aromatic ring of benzene, pyridine or pyrimidine type and the ring formed during the reaction is a nitrogenous heterocycle comprising 5 atoms of imidazole type. In the case where the nucleophile is oxygen-based ($R^7OH$), the rings obtained are benzoxazoles. The results presented were produced by preferably using two sources of different reducing agents, polymethylhydrosiloxane (PMHS), sold by Aldrich under the reference 176206, and phenylsilane ($PhSiH_3$), sold by Aldrich. In the case of the PMHS, as a silane is a polymer, the number of equivalents introduced is given with respect to the number of hydrides introduced and thus the number of monomers introduced with respect to the amine. Thus, the introduction of 3 equivalents of PMHS corresponds to the introduction of 3 equivalents of hydride and thus 3 equivalents of monomers of the PMHS with respect to the amine. Different (pre)catalysts were tested for the reaction. The general reaction scheme is as follows:

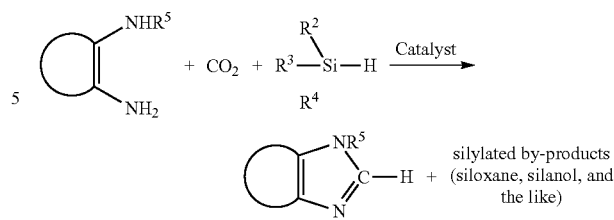

The results are shown in table 1. In all the examples of table 1, the solvent used is THF.

TABLE 1

| Amine | Silane (eq.) | (Pre)-catalyst | Catalyst equivalence | Temperature | Time | Conversion |
|---|---|---|---|---|---|---|
| benzene-1,2-diamine | PMHS 3 eq. | Carbene A | 5 mol % | 70° C. | 24 h | 90% |
| | PhSiH₃ 1 eq. | Carbene A | 5 mol % | 70° C. | 24 h | 85% |
| | PMHS 3 eq. | Cu(OAc)₂(H₂O) + dppb | 5 mol % | 100° C. | 24 h | 35% |
| benzene-1,2-diamine | PMHS 3 eq. | Carbene A | 5 mol % | 70° C. | 24 h | 90% |
| | PhSiH₃ 1 eq. | Carbene A | 5 mol % | 70° C. | 24 h | 85% |
| 3-methylbenzene-1,2-diamine | PMHS 3 eq. | Carbene A | 5 mol % | 70° C. | 24 h | 79% |
| 4,5-dimethylbenzene-1,2-diamine | PMHS 3 eq. | Carbene A | 5 mol % | 70° C. | 24 h | 50% |
| | PhSiH₃ 1 eq. | Carbene A | 5 mol % | 70° C. | 24 h | 35% |
| 4-chlorobenzene-1,2-diamine | PMHS 3 eq. | Carbene A | 5 mol % | 70° C. | 24 h | 55% |
| 4,5-dichlorobenzene-1,2-diamine | PhSiH₃ 1 eq. | Carbene A | 5 mol % | 70° C. | 24 h | 40% |
| naphthalene-2,3-diamine | PMHS 3 eq. | Carbene A | 5 mol % | 70° C. | 24 h | 39% |
| | PhSiH₃ 1 eq. | Carbene A | 5 mol % | 70° C. | 24 h | 67% |
| pyridine-2,3-diamine | PMHS 3 eq. | Carbene A | 5 mol % | 70° C. | 24 h | 35% |
| | PhSiH₃ 1 eq. | Carbene A | 5 mol % | 70° C. | 24 h | 72% |
| pyridine-3,4-diamine | PMHS 3 eq. | Carbene A | 5 mol % | 70° C. | 24 h | 21% |
| | PMHS 3 eq. | Carbene A | 5 mol % | 100° C. | 24 h | 40% |
| | PhSiH₃ 1 eq. | Carbene A | 5 mol % | 70° C. | 24 h | 50% |

TABLE 1-continued

| Amine | Silane (eq.) | (Pre)-catalyst | Catalyst equivalence | Temperature | Time | Conversion |
|---|---|---|---|---|---|---|
| pyrimidine-4,5-diamine | PhSiH$_3$ 1 eq. | Carbene A | 5 mol % | 70° C. | 24 h | 28% |
| N-methyl-benzene-1,2-diamine | PMHS 3 eq. | Carbene A | 5 mol % | 70° C. | 24 h | 74% |
| N-phenyl-benzene-1,2-diamine | PMHS 3 eq.<br>PhSiH$_3$ 1 eq. | Carbene A<br>Carbene A | 5 mol %<br>5 mol % | 70° C.<br>70° C. | 24 h<br>24 h | 72%<br>65% |
| 2-aminophenol | PMHS 3 eq. | Carbene A | 5 mol % | 70° C. | 24 h | 14% |

The results show that, under the operating conditions shown in table 1, the CO$_2$ can be converted with good yields, indeed even very good (>70%) yields, into nitrogenous heterocycles in which all the C=O bonds of the CO$_2$ have been replaced, in the presence of an organic catalyst.

B—Synthesis of 4-Quinazolinone Derivatives from Functionalized Aromatic Amines

The following results describe the synthesis of 4-quinazolinone derivatives from aromatic amines functionalized in ortho position by amides (anthranilamides). In this case, the amine R$^1$NH$_2$ and the nitrogenous nucleophile R$^5$R$^6$NH (in this case an amide) are two reactive functional groups of one and the same molecule (diamine) and are thus connected via a covalent bond. This bond is preferably an aromatic ring of benzene, pyridine or pyrimidine type and the ring formed during the reaction is a nitrogenous heterocycle comprising 6 atoms. The results presented in table 2 were obtained by preferably using polymethylhydrosiloxane (PMHS) as reducing agent, the latter proving to be more effective with regard to these reactants than phenylsilane (PhSiH$_3$).

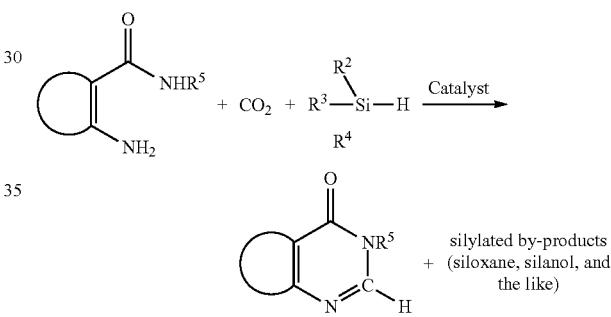

The results, under the operating conditions described, are shown in table 2. In all the examples of table 2, the solvent used is THF.

TABLE 2

| Amine | Silane (eq.) | Catalyst | Catalyst equivalence | Temperature | Time | Conversion |
|---|---|---|---|---|---|---|
| anthranilamide | PMHS 3 eq.<br>PMHS 6 eq.<br>PhSiH$_3$ 1 eq.<br>PMHS 3 eq. | Carbene A<br>Carbene A<br>Carbene A<br>Cu(OAc)$_2$(H$_2$O) + dppb | 5 mol %<br>5 mol %<br>5 mol %<br>5 mol % | 70° C.<br>70° C.<br>100° C.<br>100° C. | 24 h<br>24 h<br>24 h<br>24 h | 65%<br>85%<br>50%<br>30% |
| anthranilamide | PMHS 3 eq.<br>PMHS 6 eq.<br>PhSiH$_3$ 1 eq. | Carbene A<br>Carbene A<br>Carbene A | 5 mol %<br>5 mol %<br>5 mol % | 70° C.<br>70° C.<br>100° C. | 24 h<br>24 h<br>24 h | 65%<br>85%<br>50% |

TABLE 2-continued

| Amine | Silane (eq.) | Catalyst | Catalyst equivalence | Temperature | Time | Conversion |
|---|---|---|---|---|---|---|
| 2-amino-N-methylbenzamide | PMHS 3 eq. | Carbene A | 5 mol % | 70° C. | 24 h | 27% |
| 2-amino-N-benzylbenzamide | PMHS 3 eq. | Carbene A | 5 mol % | 70° C. | 24 h | 34% |
| 2-amino-N-phenylbenzamide | PMHS 3 eq. | Carbene A | 5 mol % | 70° C. | 24 h | 56% |

These 4-quinazolinone derivatives exhibit a specific synthetic interest since they constitute units commonly employed in the development of medicaments.

C—Synthesis of 3,4-Dihydroquinazoline Derivatives from 2-Aminobenzylamines

The following results for their part describe the synthesis of 3,4-dihydroquinazoline derivatives from 2-aminobenzylamines. In this case, the amine $R^1NH_2$ and the nitrogenous nucleophile $R^5R^6NH$ are two reactive functional groups of one and the same molecule (diamine) and are thus connected by a covalent bond and the ring formed during the reaction is a nitrogenous heterocycle comprising 6 atoms. The results presented in table 3 were obtained by using preferably two sources of different reducing agents, polymethylhydrosiloxane (PMHS) and phenylsilane ($PhSiH_3$).

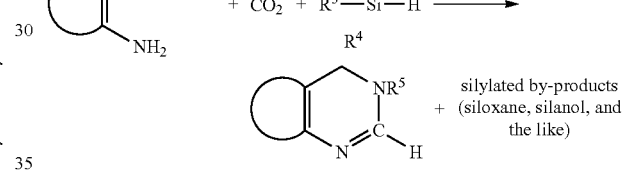

The results are shown in table 3. In all the examples of table 3, the solvent used is THF.

TABLE 3

| Amine | Silane (eq.) | Catalyst | Catalyst equivalence | Temperature | Time | Conversion |
|---|---|---|---|---|---|---|
| 2-aminobenzylamine | PMHS 3 eq. | Carbene A | 5 mol % | 70° C. | 24 h | 33% |
| | PhSiH₃ 1 eq. | Carbene A | 5 mol % | 100° C. | 24 h | 5% |
| | PMHS 3 eq. | Cu(OAc)₂(H₂O) + dppb | 5 mol % | 100° C. | 24 h | 10% |
| 2-aminobenzylamine | PMHS 3 eq. | Carbene A | 5 mol % | 70° C. | 24 h | 33% |
| | PhSiH₃ 1 eq. | Carbene A | 5 mol % | 100° C. | 24 h | 5% |
| N-benzyl-2-aminobenzylamine | PMHS 3 eq. | Carbene A | 5 mol % | 70° C. | 24 h | 60% |

TABLE 3-continued

| Amine | Silane (eq.) | Catalyst | Catalyst equivalence | Temperature | Time | Conversion |
|---|---|---|---|---|---|---|
| 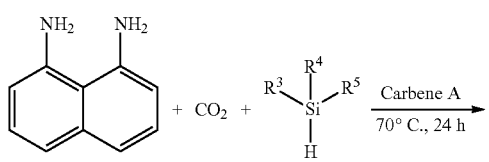 | PMHS 3 eq. | Carbene A | 5 mol % | 70° C. | 24 h | 56% |

The results show that, under the operating conditions shown in table 3, it is possible to form, according to the process of the invention, nonaromatic nitrogenous heterocycles.

D—Synthesis of 8-Aminonaphthylamine

The process of the invention has been used for the synthesis of 8-aminonaphthylamine according to the operating conditions shown in the following scheme. The distinguishing feature of the starting amine is that the amine functional groups are carried by two different aromatic nuclei. The silane used is phenylsilane ($PhSiH_3$).

case, the amine $R^1NH_2$ and the nucleophilic agent $R^5R^6NH$ are two distinct molecules, which may or may not be identical in order to obtain symmetrical or asymmetrical formamidines. The results presented in table 4 were obtained by using preferably phenylsilane ($PhSiH_3$).

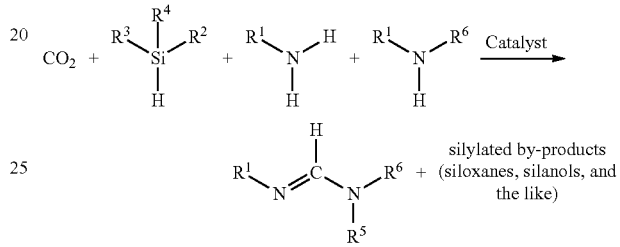

The results are shown in table 4. The solvent used in this example is THF.

TABLE 4

| Amine | Silane (eq.) | Catalyst | Catalyst equivalence | Temperature | Time | Conversion to formamidine PhN=CH—NHPh |
|---|---|---|---|---|---|---|
| 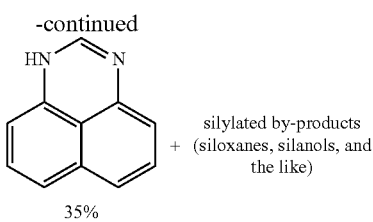 | $PhSiH_3$ 1 eq. | TBD | 5 mol % | 100° C. | 24 h | 28% |
| | $PhSiH_3$ 1 eq. | TBD | 5 mol % | 100° C. | 48 h | 30% |
| | $PhSiH_3$ 0.6 eq. | TBD | 5 mol % | 100° C. | 48 h | 44% |
| | $PhSiH_3$ 1 eq. | $Cu(OAc)_2 \cdot (H_2O) + dppb$ | 5 mol % | 100° C. | 24 h | 36% |
| | PMHS 3 eq. | $Cu(OAc)_2 \cdot (H_2O) + dppb$ | 5 mol % | 100° C. | 24 h | 70% |
| | $PhSiH_3$ 1 eq. | $Fe(BF_4)_2 \cdot 6H_2O_6 + PP_3$ | 5 mol % | 100° C. | 24 h | 26% |
| | $PhSiH_3$ 2 eq. | $Fe(acac)_3 + PP_3$ | 5 mol % | 100° C. | 24 h | 15% |
| | $PhSiH_3$ 2 eq. | $ZnEt_2$ | 10 mol % | 100° C. | 24 h | 6% |
| $C_7H_{15}NH_2$ | $PhSiH_3$ 1 eq. | $Fe(BF_4)_2 \cdot 6H_2O_6 + PP_3$ | 5 mol % | 100° C. | 24 h | 50% |
| 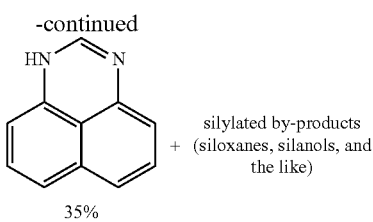 (benzyl) | $PhSiH_3$ 1 eq. | $Fe(BF_4)_2 \cdot 6H_2O_6 + PP_3$ | 5 mol % | 100° C. | 24 h | 52% |
| | $PhSiH_3$ 2 eq. | $Fe(acac)_3 + PP_3$ | 5 mol % | 100° C. | 24 h | 5% |

E—Synthesis of Formamidine Derivatives from Mixtures of Amines

The following results for their part describe the synthesis of formamidine derivatives from mixtures of amines. In this The results show that, under the operating conditions shown in table 4, it is not necessary for the amine of formula (II) and the nucleophilic agent of formula (IV) to be carried by the same molecule. It is thus possible to form, according to the process of the invention, noncyclic formamidines.

The abbreviations used in these examples are represented below:

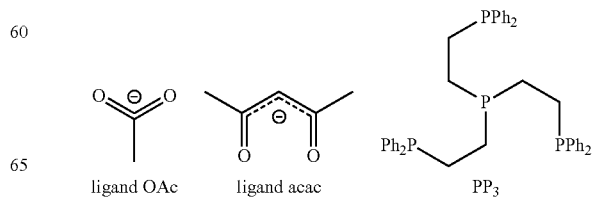

ligand OAc    ligand acac    $PP_3$

-continued

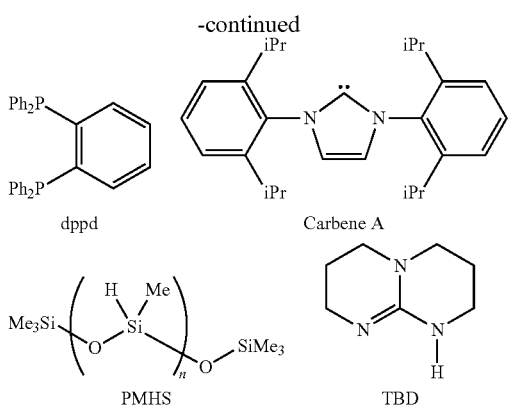

The invention claimed is:

1. A process for the preparation of nitrogenous compounds of formula (I):

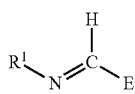

in which:
R$^1$ represents a hydrogen atom, an alkyl group, an alkenyl group, an alkynyl group, an aryl group, a heteroaryl group, a heterocycle, a carbonyl (—CO—) group, a silyl group, a siloxy group or an amino group, said alkyl, alkenyl, alkynyl, aryl, heteroaryl, heterocycle, silyl, siloxy and amino groups being optionally substituted,
R$^1$ optionally comprises an H, C, N, O, F, Si and/or S as defined below;
H represents a hydrogen atom ($^1$H), deuterium ($^2$H) or tritium ($^3$H);
C represents a carbon atom ($^{12}$C) or a $^{11}$C, $^{13}$C or $^{14}$C isotope;
N represents a nitrogen atom ($^{14}$N) or a $^{15}$N isotope;
O represents an oxygen atom ($^{16}$O) or an $^{18}$O isotope;
F represents a fluorine atom ($^{19}$F) or a $^{18}$F isotope;
Si represents a silicon atom ($^{28}$Si) or a $^{29}$Si or $^{30}$Si isotope;
S represents a sulfur atom ($^{32}$S) or a $^{33}$S, $^{34}$S or $^{36}$S isotope;
E represents an R$^5$R$^6$N— or R$^7$O— group with
R$^5$, R$^6$ and R$^7$ representing, independently of one another, a hydrogen atom, an alkyl group, an alkenyl group, an alkynyl group, an aryl group, a heteroaryl group, a heterocycle, a (—(CO)—) group, a silyl group, a siloxy group or an amino group, said alkyl, alkenyl, alkynyl, aryl, heteroaryl, heterocycle, silyl, siloxy and amino groups being optionally substituted, or
R$^5$ and R$^6$, taken together with the nitrogen atom to which they are bonded, form an optionally substituted heterocycle, or
R$^1$ and R$^5$, taken together with the two nitrogen atoms to which they are respectively bonded, form an optionally substituted heterocycle, or
R$^1$ and R$^7$, taken together with the nitrogen atom and oxygen atom to which they are respectively bonded, form an optionally substituted heterocycle, R$^5$, R$^6$ and R$^7$ optionally comprise an H, C, N, O, F, Si and/or S as defined above,
R$^1$, N and O being as defined above;
comprising a step of reacting an amine of formula (II):

in which R$^1$ and N are as defined above, with CO$_2$, in which C and O are as defined above, in the presence:
of a catalyst,
of a silane compound of formula (III):

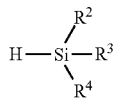

in which:
H is as defined above,
R$^2$, R$^3$ and R$^4$ represent, independently of one another, a hydrogen atom, a halogen atom, a hydroxyl group, an alkyl group, an alkenyl group, an alkynyl group, an alkoxy group, a silyl group, a siloxy group, an aryl group or an amino group, said alkyl, alkenyl, alkynyl, alkoxy, silyl, siloxy, aryl and amino groups being optionally substituted, or
R$^4$ is as defined above and R$^2$ and R$^3$, taken together with the silicon atom to which they are bonded, form an optionally substituted silylated heterocycle, and of a nucleophilic agent of formula (IV):

E-H (IV)

in which E is as defined above and H is a hydrogen atom.

2. The process as claimed in claim 1, wherein in the amine of formula (II), R$^1$ represents a hydrogen atom, an alkyl group, an aryl group, a heteroaryl group, a heterocycle or an amino group, said alkyl, amino, aryl, heterocycle and heteroaryl groups optionally being substituted.

3. The process as claimed in claim 1, wherein, in the silane compound of formula (III), R$^2$, R$^3$ and R$^4$ represent, independently of one another, a hydrogen atom, an alkyl group, an alkoxy group, an aryl group, a silyl group or a siloxy group, said alkyl, alkoxy, silyl, siloxy and aryl groups optionally being substituted.

4. The process as claimed in claim 1, wherein the nucleophilic agent E-H of formula (IV), E represents an R$^5$R$^6$N— group with
R$^5$ and R$^6$ representing, independently of one another, a hydrogen atom, an alkyl group, an aryl group, a heteroaryl group, a heterocycle or an amino group, said alkyl, aryl, heteroaryl, heterocycle and amino groups optionally being substituted, or
R$^5$ and R$^6$, taken together with the nitrogen atom to which they are bonded, form an optionally substituted heterocycle.

5. The process as claimed in claim 1, wherein the catalyst is selected from the group consisting of organic catalysts and metal catalysts chosen from metal salts or complexes.

6. The process as claimed in claim 5, wherein the organic catalyst is:

a secondary or tertiary amine, selected from the group consisting of triazabicyclodecene (TBD), N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt and N-diisopropylethylamine (DIPEA or DIEA), or an N-heterocyclic carbene resulting from an imidazolium salt selected from the group consisting of 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di(tert-butyl)-1H-imidazol-3-ium (carbene F) and 1,3-di(tert-butyl)-4,5-dihydro-1H-imidazol-3-ium salts, said salts being in the form of chloride salts.

7. The process as claimed in claim 5, wherein the metal catalyst is selected from the group consisting of the salts or complexes of:

metals chosen from boron, silicon, aluminum, gallium, tin or indium;

alkali metals chosen from sodium or potassium;

alkaline earth metals chosen from magnesium or calcium;

transition metals selected from the group consisting of nickel, iron, cobalt, zinc, copper, rhodium, ruthenium, platinum, palladium and iridium; and rare earth metals chosen from lanthanum, cerium, praseodymium or neodymium.

8. The process as claimed in claim 1, wherein the reaction is carried out under a $CO_2$ pressure of between 1 and 50 bar, limits included.

9. The process as claimed in claim 1, wherein the reaction is carried out at a temperature of between 25 and 150° C., limits included.

10. The process as claimed in claim 1, wherein the reaction is carried out for a period of time of 5 minutes to 72 hours, limits included.

11. The process as claimed in claim 1, wherein the reaction is carried out in a mixture of at least two solvent(s) sleeted from the group consisting of:

ethers, hydrocarbons, nitrogenous solvents, sulfoxides, and alkyl halides.

12. The process as claimed in claim 1, wherein the molar ratio of the silane compound of formula (III) to the amine of formula (II) is from 1 to 10, limits included.

13. The process as claimed in claim 1, wherein the amount of catalyst is from 0.001 to 1 molar equivalent, limits included, with respect to the amine of formula (II).

14. A process for the preparation of formamide compounds of formula (I) as claimed in claim 1 in the manufacture of vitamins, pharmaceutical products, adhesives, acrylic fibers, synthetic leather, pesticides, herbicides, antifungals and fertilizers.

15. A process for the manufacture of tracers and radioactive tracers, wherein the process comprises a step of preparation of nitrogenous compounds of formula (I) by the process as claimed in claim 1.

16. The process as claimed in claim 1, wherein the reaction is carried out under a $CO_2$ pressure of between 1 and 30 bar, limits included.

17. The process as claimed in claim 1, wherein the reaction is carried out under a $CO_2$ pressure of between 1 and 10 bar, limits included.

18. The process as claimed in claim 1, wherein the reaction is carried out at a temperature of between 50 and 125° C., limits included.

19. The process as claimed in claim 1, wherein the reaction is carried out for a period of time of 15 minutes to 48 hours.

20. The process as claimed in claim 1, wherein the reaction is carried out in a of a mixture of at least two solvent(s) selected from the group consisting of diethyl ether, THF, benzene, toluene, pyridine, acetonitrile, dimethyl sulfoxide, chloroform, and methylene chloride.

* * * * *

UNITED STATES PATENT AND TRADEMARK OFFICE
CERTIFICATE OF CORRECTION

| | | |
|---|---|---|
| PATENT NO. | : 9,133,135 B2 | Page 1 of 1 |
| APPLICATION NO. | : 14/404885 | |
| DATED | : September 15, 2015 | |
| INVENTOR(S) | : Cantat et al. | |

It is certified that error appears in the above-identified patent and that said Letters Patent is hereby corrected as shown below:

In the claims:

Column 32,
Line 2, "sleeted" should read --selected--;
Line 36, "in a of a" should read --in a--.

Signed and Sealed this
Fifteenth Day of March, 2016

Michelle K. Lee
*Director of the United States Patent and Trademark Office*